(12) United States Patent
Yao et al.

(10) Patent No.: US 10,344,224 B2
(45) Date of Patent: Jul. 9, 2019

(54) IMPROVING CATALYST LIFETIME

(71) Applicant: PHILLIPS 66 COMPANY, Houston, TX (US)

(72) Inventors: Jianhua Yao, Bartlesville, OK (US); Bruce B. Randolph, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 191 days.

(21) Appl. No.: 14/966,705

(22) Filed: Dec. 11, 2015

(65) Prior Publication Data

US 2016/0176777 A1    Jun. 23, 2016

Related U.S. Application Data

(60) Provisional application No. 62/094,339, filed on Dec. 19, 2014.

(51) Int. Cl.

| | |
|---|---|
| *C10G 50/00* | (2006.01) |
| *B01J 29/40* | (2006.01) |
| *B01J 35/00* | (2006.01) |
| *B01J 35/02* | (2006.01) |
| *B01J 35/10* | (2006.01) |
| *C07C 2/02* | (2006.01) |
| *C07C 2/06* | (2006.01) |
| *C07C 2/12* | (2006.01) |
| *C07C 2/00* | (2006.01) |
| *C07C 2/08* | (2006.01) |
| *C07C 2/04* | (2006.01) |

(52) U.S. Cl.
CPC .............. *C10G 50/00* (2013.01); *B01J 29/40* (2013.01); *B01J 35/002* (2013.01); *B01J 35/023* (2013.01); *B01J 35/109* (2013.01); *B01J 35/1042* (2013.01); *B01J 35/1057* (2013.01); *B01J 35/1061* (2013.01); *C07C 2/00* (2013.01); *C07C 2/02* (2013.01); *C07C 2/04* (2013.01); *C07C 2/06* (2013.01); *C07C 2/08* (2013.01); *C07C 2/12* (2013.01); *B01J 2229/42* (2013.01)

(58) Field of Classification Search
None
See application file for complete search history.

(56) References Cited

U.S. PATENT DOCUMENTS

| | | | | |
|---|---|---|---|---|
| 4,560,536 A | * | 12/1985 | Tabak | C07C 2/12 208/135 |
| 2016/0136625 A1 | * | 5/2016 | Haw | B01J 35/1061 585/653 |

OTHER PUBLICATIONS

Concoa, https://www.concoa.com/ethylene_properties.html, accessed Jun. 22, 2017.*

* cited by examiner

*Primary Examiner* — In Suk C Bullock
*Assistant Examiner* — Ali Z Fadhel
(74) *Attorney, Agent, or Firm* — Phillips 66 Company

(57) ABSTRACT

A process for converting ethylene to liquid fuel products having substantially improved catalyst life. The catalyst has small zeolite crystallites and high pore volume to produce ethylene oligomerization and reduce coke production at productive temperature, pressure and flow rates.

5 Claims, 8 Drawing Sheets

IMPROVING CATALYST LIFETIME

CROSS-REFERENCE TO RELATED APPLICATIONS

This application is a non-provisional application which claims benefit under 35 USC § 119(e) to U.S. Provisional Application Ser. No. 62/094,339 filed Dec. 19, 2014, entitled "Improving Catalyst Lifetime," which is incorporated herein in its entirety.

STATEMENT REGARDING FEDERALLY SPONSORED RESEARCH OR DEVELOPMENT

None.

FIELD OF THE INVENTION

This invention relates to converting raw ethylene to fuel and especially to enhancing the catalyst lifetime for a practical implementation of catalytic conversion process.

BACKGROUND OF THE INVENTION

The US shale gas boom has resulted in a significant increase in natural gas production as well as a significant increase in the production of natural gas liquids. One of the main components of the natural gas liquids produced with natural gas is ethane. Ethane is most commonly used as petrochemical feedstock such as for the production of ethylene. Ethylene is a feedstock for many, many high volume chemical based products such as polyethylene and styrene plastics, among many others. However, there are no other sizable consumption markets for ethane. US ethane supplies currently exceed demand by about 300,000 barrels per day causing depressed prices for ethane and attracting considerable investment into new ethane to ethylene production facilities. Most supply/demand estimates indicate that ethane will remain in surplus for many years and these predictions take in to account the new ethane to ethylene conversion capacity being built. Therefore, new markets for ethane and new technologies for converting ethane to products that have large existing or substantially growing demand would be very attractive in light of the projected low prices for ethane for many years. One of the largest end use markets is liquid transportation fuel and a simple conversion technology to any transportation fuel could prove to be quite profitable.

So, with the expectation that ethane will be plentiful and cheap, old technologies are being reconsidered that use ethane as a feedstock. One old technology is the conversion of ethane to current fuel markets such as gasoline and/or diesel. However, while there are known chemical processes for converting ethane to gasoline and or diesel, it has yet to be put into commercial production. With excess ethane currently being produced, there is or will soon be a need to create commercially viable processes to convert ethane to liquid transportation fuels.

BRIEF SUMMARY OF THE DISCLOSURE

The invention more particularly relates to oligomerizing ethylene to transportation fuel products in a reactor with a fixed bed of ZSM-5 catalyst that is essentially free of catalyst metals other than silica and alumina. The ZSM-5 catalyst has zeolite crystallites with a mean length of less than 150 nm and a total pore volume greater than 0.60 ml/g. The oligomerizing process is conducted at a pressure between 0 psig and 800 psig, a temperature of between 260 and 420° C., and a gas hourly space velocity of between 1000 and 5000 inverse hours wherein at least 85% of the ethylene is converted.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

Figure 1:
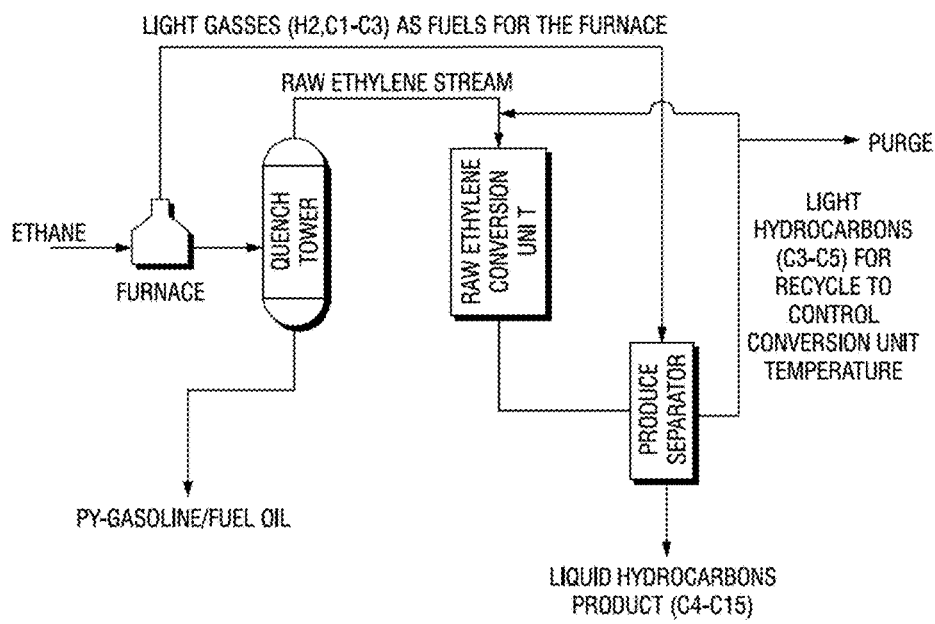
FIG. 1 is a schematic drawing of a reactor for the present invention.

Ethane may be converted to liquid transportation fuel in a process 10 shown schematically in FIG. 1. Ethane from an ethane stream 12 is fed directly into a cracking furnace 14. The process of cracking ethane is typically an uncatalyzed process relying on pressure and temperature in a furnace, such as cracking furnace 14. However, there are catalytic processes for cracking ethane that are acceptable for the present invention. The cracking furnace 14 produces a number products primarily including hydrogen, ethylene, water, methane, and unconverted ethane, but also including small amounts of propylene, acetylene and butadiene, along with trace amounts of other hydrocarbons. All of these products are suitable for conversion in an ethylene oligomerizer in accordance with the present invention.

The products from the cracking furnace 14 are fed directly to a quench tower 16 via a furnace conduit 15 to stop further thermal reactions. A liquid product is taken from the bottom of the quench tower 16 via drain 18 comprising gasoline and fuel oil density materials that may be fed to a refinery. The bulk of the products are vaporous under the conditions in the quench tower 16 and exit the top via overhead conduit 17. The bulk of the products comprise raw ethylene along with the other lighter products described above.

The raw ethylene stream is fed into a catalytic oligomerization reactor 20. The catalytic oligomerization reactor 20 includes a fixed bed of catalyst to convert the raw ethylene stream into a number of products primarily including a gasoline product having an octane rating of about 88. The products from the catalytic oligomerization reactor 20 are conveyed via an outlet conduit to a product separator 22 to separate the products into at least three streams or cuts. A bottom cut comprising a stream of C4 to C15 hydrocarbon molecules that exits the bottom via product conduit 23. These are the valuable products that may be blended into current liquid transportation fuels such as gasoline and perhaps diesel or jet fuel.

The top cut comprises light gases such as hydrogen and C1 to C3 hydrocarbons that are conveyed back to the furnace 14 via light gas conduit 24. These light gases are burned in the furnace 14 to generate heat or supplemental heat for cracking the ethane. A middle cut comprising light hydrocarbons having a C3 to C5 chain length exits middle cut conduit 26. The light hydrocarbons may be recycled to the catalytic oligomerization reactor 20 via recycle conduit 27 or may be purged from the system 10 via purge line 28. If the middle cut is to be purged, it is preferably directed into a refinery stream or to a NGL fractionator for capture and sale.

This process is fairly simple with one well known and well understood unit (the furnace 14), and a second unit (the oligomerization reactor 20) that been considered over the years. Interestingly, in current studies, although there are other products in the feed stream to the catalytic oligomerization reactor 20, in early tests, about 98% of the ethylene was converted and over 75% of the products from the ethylene converted to C5+ materials. This is very exciting. With ethane prices very depressed and gasoline prices being among the highest priced non-specialty refinery products, this conversion technology could prove to be quite profitable. However, there is a down side. The down side is that although there are quite a number of known catalysts for the catalytic process of oligomerizing ethylene, the catalyst life of these catalysts is desperately short for a commercial system. Many catalysts have been tested. The best results so far have been accomplished with ZSM-5 catalysts, but the catalyst life of ZSM-5 catalysts still has been measured in hours. Basically, the catalysts tend to coke up pretty fast. The catalysts may be regenerated through conventional oxidation by burning the coke off the catalyst, but such short catalyst life will cause substantial operating costs. While the current price spread between ethane and gasoline is huge and very attractive, price spreads will change over time most likely shrinking and not expanding. With high operating costs, even a marginal reduction in price spread could substantially reduce or eliminate any profitability of such a commercial system.

Figure 2:
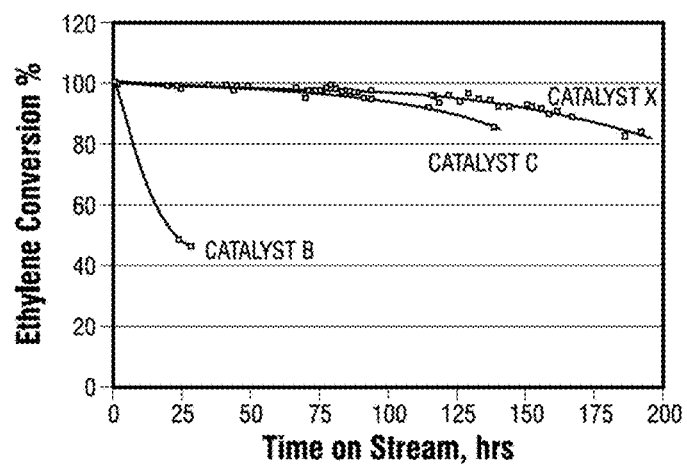
FIG. 2 is a chart showing catalyst life for ethylene conversion in the schematic process according to FIG. 1 for various catalysts.

Focusing on catalyst life, commercial catalysts B and C were tested in a bench scale reactor at 50 psig and 310° C. High conversion of the ethylene was the focus and as shown in FIG. 2, Catalyst B lost substantial conversion productivity right away while Catalyst C maintained high conversion. High conversion for only 100 hours is probably quite a bit short of being suitable for commercial operation.

Figure 3:
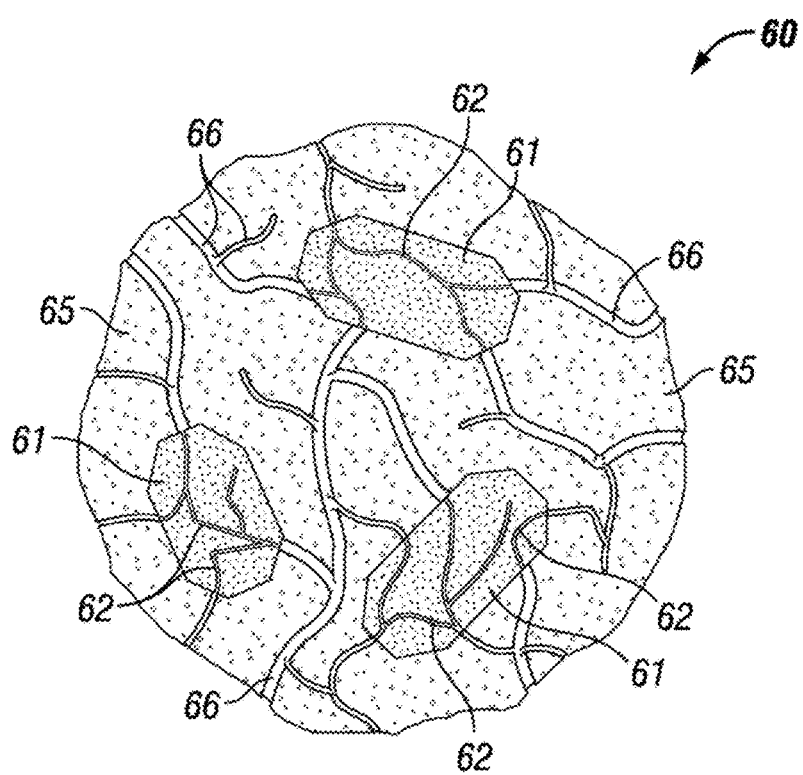
FIG. 3 is a diagram showing a simplified representation of what is believed to be the structure of the catalyst.

The loss of conversion in the process is from coke formation. Avoiding coke formation would likely increase catalyst life. The process of forming coke in this reaction process is actually a multistep reaction process that begins with oligomerization, then proceeds to cyclization, then to poly-nuclear cyclization and then finally to coke. Recognizing that our desired reaction occurs first and our undesired reaction occurs last suggested that we need to stop the reaction between the first and last reactions. While there may be many ways to stop the reaction halfway through such a sequential process, since it was recognized that these reactions are occurring on the Bronsted acid sites within the micropore of the ZSM-5 catalyst crystallite, that pushing the reactants through the micropores faster might reduce the productivity of coke on the acid sites. This eventually led to reducing the size or more specifically, the length of the micropores to reduce the opportunities or probabilities for forming coke. Looking at FIG. 3, a catalyst particle 60 (or actually a portion of a catalyst particle) is shown. The catalyst particle includes a number of ZSM-5 crystallites 61. The crystallites tend to be fairly small and are captured within an alumina binder 65. The binder 65 includes catalyst pores 66. The catalyst pores have various lengths, widths and volumes. Many are blind channels, but some lead to the crystallites 61. Within the crystallites 61 are micropores 62. These micropores have highly predictive width or diameter and that is in the nature of ZSM-5. However, the crystallites may be formed or extruded into various sizes.

For this present invention, very, very small crystallites are believed to provide an advantage for catalyst life in the proposed reaction because smaller crystallites would have shorter length micropores. As such, the products of the first reaction tend to be exposed to the Bronsted acid sites for a very brief time as the materials move through the shorter length micropores. As noted above, the desired reaction is to convert the ethylene to liquid hydrocarbons on the Bronsted acid sites and the following reactions to produce coke and coke precursor from aromatics are undesirable. A second aspect of the invention is that the catalyst pores 66 are desired to be extra-large. Larger catalyst pores 66 would seem to allow quick diffusion of produced hydrocarbons and reduce coking propensity. Once a longer chain hydrocarbon is formed and passes into a catalyst pore of large diameter, such products are less likely to re-enter another micropore because the product molecules have been allowed to expand out to their natural dimension in such large catalyst pores 66. Once such large molecules have opened up, the reactants will be preferentially allowed into the micropores 62 due to their much smaller size and the likelihood that the larger product molecules will have to deform somewhat to fit into the micropores. Specifically, it is believed that crystallite sizes will need to be less than 500 nm, but smaller is preferred. Crystallite sizes below 150 nm are more attractive, but small crystallites need to be combined with other catalyst attributes to obtain the desired catalyst life.

As seen in Table 1 below and FIGS. 6, 7, 8, and 9, Catalyst C has smaller crystallites than Catalyst B.

A second observation underlying the present invention is that while it is necessary to bind the ZSM-5 into pellets or other structure to contain the catalyst in a fixed bed, that the size of the mesopores in the binder may designed to alter the diffusion patterns of the reactants and products within the pellets to reduce the likelihood that an oligomerized product will be allowed to continue in a second micropore and form coke within the second micropore. Ultimately, it is believed that large mesopores in the pellet binder combined with small crystallites reduces the productivity of coke. As such, this catalyst would require less frequent regeneration.

Figure 10:
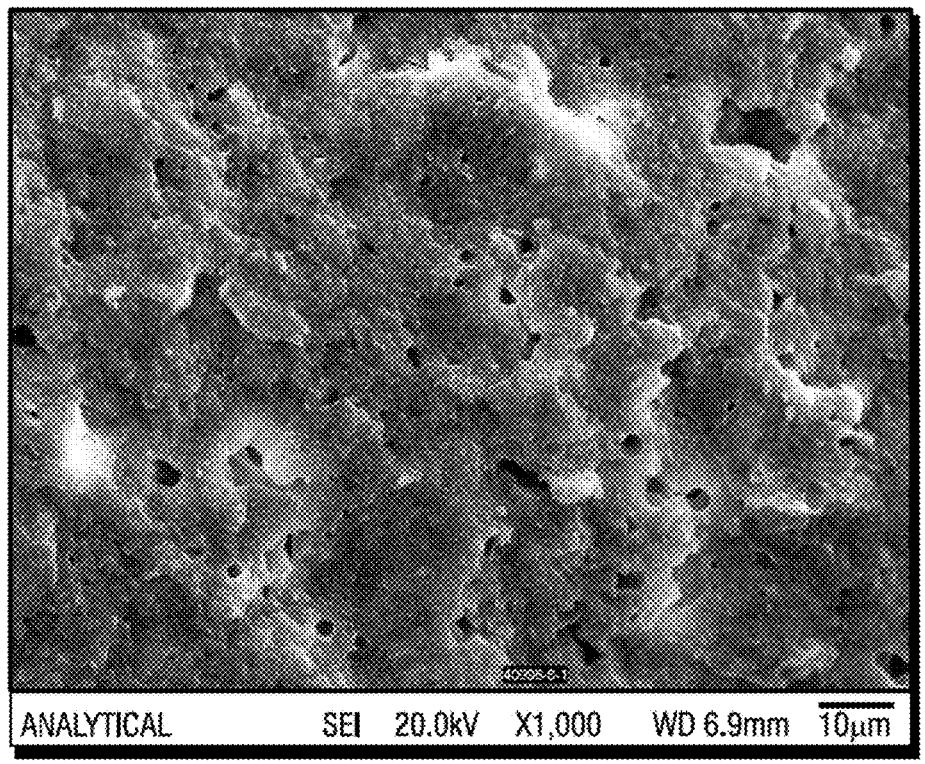
FIG. 10 is a scanning electron microscope photograph of Catalyst C at 1000 magnification to show the mesopores in the binder of the catalyst particles.
Figure 11:
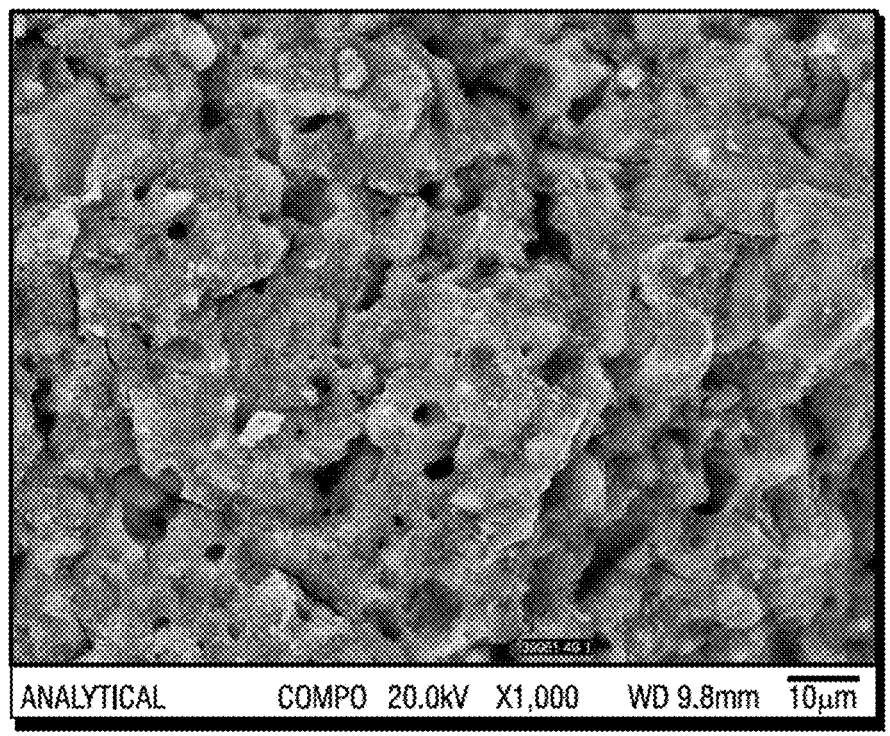
FIG. 11 is a scanning electron microscope photograph of Catalyst X at 1000 magnification to show the enlarged mesopores in the binder of the catalyst particles.

To test this theory, an inventive Catalyst X was prepared using crystallites that are small like Catalyst C. The surface area and pore volume were determined by nitrogen adsorption. Catalyst morphology was examined by SEM showing much larger crystal size for Catalyst B (see FIG. 6) as compared with Catalyst C (see FIGS. 8 and 10). Using Catalyst C as a hurdle target, Catalyst X was designed to have higher surface area and higher pore volume (see FIG. 11). As seen in FIG. 2, the catalyst life increased by about 40% over the life of Catalyst C.

TABLE 1

|  | Surface Area | | | Pore Volume | | |
| --- | --- | --- | --- | --- | --- | --- |
|  | BET Surface Area (m²/g) | Micropore Surface Area (m²/g) | "External" Surface Area (m²/g) | Micropore Volume (ml/g) | Total Pore Volume (ml/g) | Crystallite Size (nm) |
| Cat B | 377 | 266 | 111 | 0.120 | 0.29 | ~500 |
| Cat C | 365 | 192 | 173 | 0.083 | 0.56 | <~150 |
| Cat X | 410 | 267 | 143 | 0.115 | 0.67 | <~150 |

It would appear that catalyst having a crystallite size of less than 150 nm and a total pore volume greater than 0.60 ml/g will have a better and longer catalyst life prior to regeneration for the proposed process. Other factors of interest include having a micropore volume of greater than 0.08 ml/g in the catalyst and also having an external surface area of at least 135 m²/g appear to lend to longer catalyst life.

The tests were performed under the conditions shown in Table 2 with a representative product slate and performance. These conditions are believed to be much harsher than one would expect to run the system of FIG. 1 in a commercial setting. The harsher conditions were intended to stress the catalysts and assess the expected catalyst life. However, five days under the harsh conditions is still well short of desired where threshold catalyst life would hopefully be six months or longer. Initial hurdle considerations for commercial viability are believed to be about 10 days of catalyst life before regeneration is necessary and at least one year before replacement assuming many cycles of reaction and regeneration.)

TABLE 2

| Pressure, psig | 50 |
| --- | --- |
| Temperature, Degrees Celsius | 310 |
| Ethylene conversion, % | 98 |
| HC product selectivity, wt % | |
| Methane | 0.1 |
| Ethane | 0.8 |
| Propane | 2.1 |
| Propylene | 1.9 |
| Butanes | 9.3 |
| Butenes | 5.5 |
| C5+ | 80.2 |
| Total, % | 100.00 |

Figure 4:
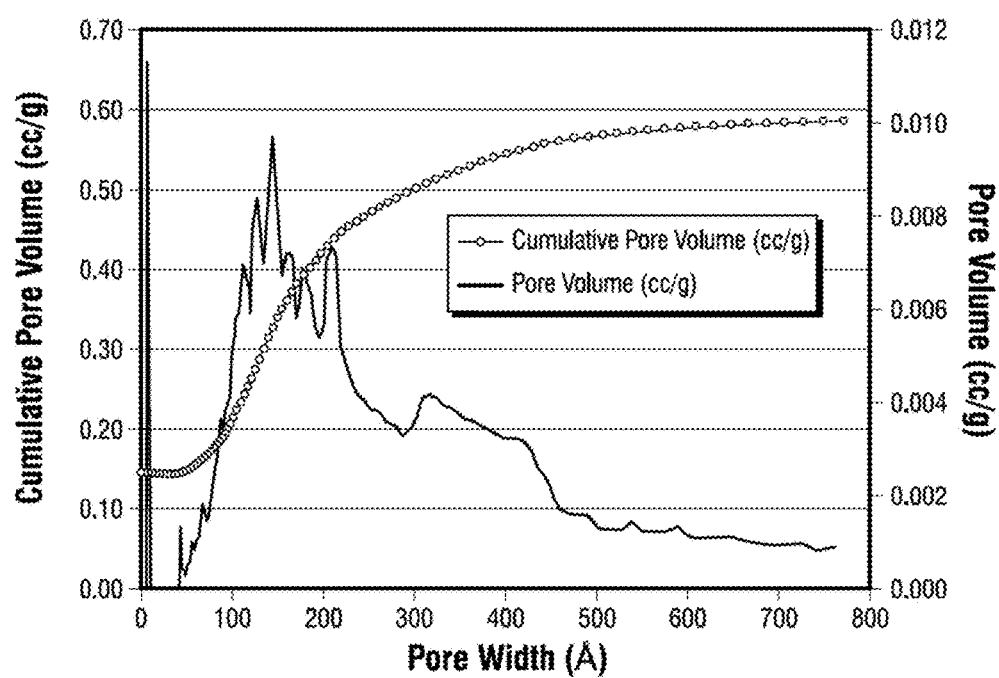
FIG. 4 is a chart showing pore volume and diameter of known ZSM-5 catalyst shown as Catalyst C in FIG. 2.
Figure 5:
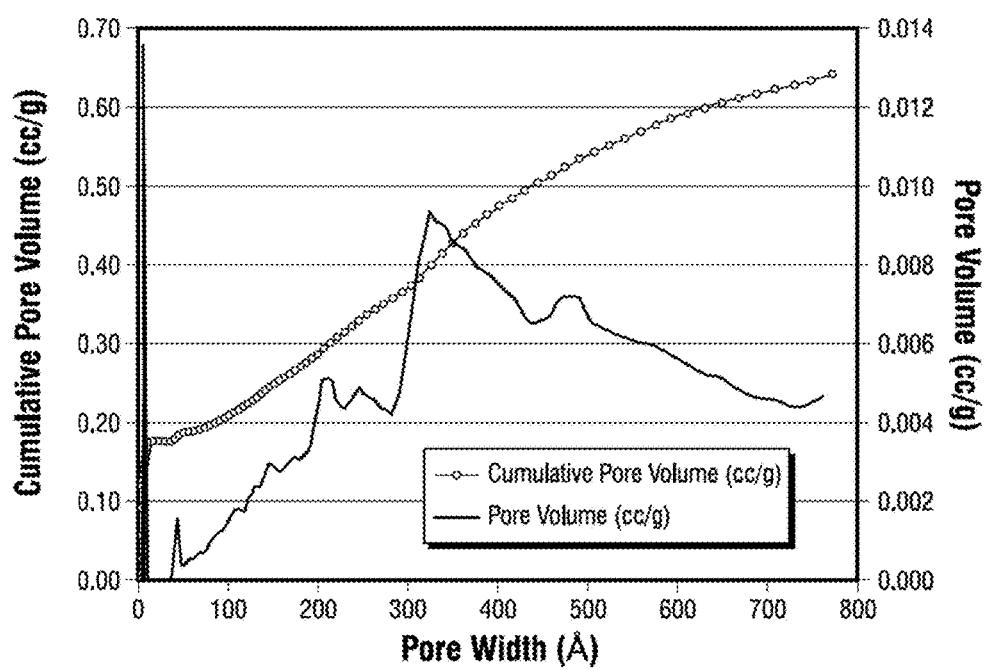
FIG. 5 is a chart also showing pore volume and diameter of an inventive Catalyst X which suggests the desired attributes of catalyst that will provide practical catalyst life for the proposed catalytic process.
Figure 6:
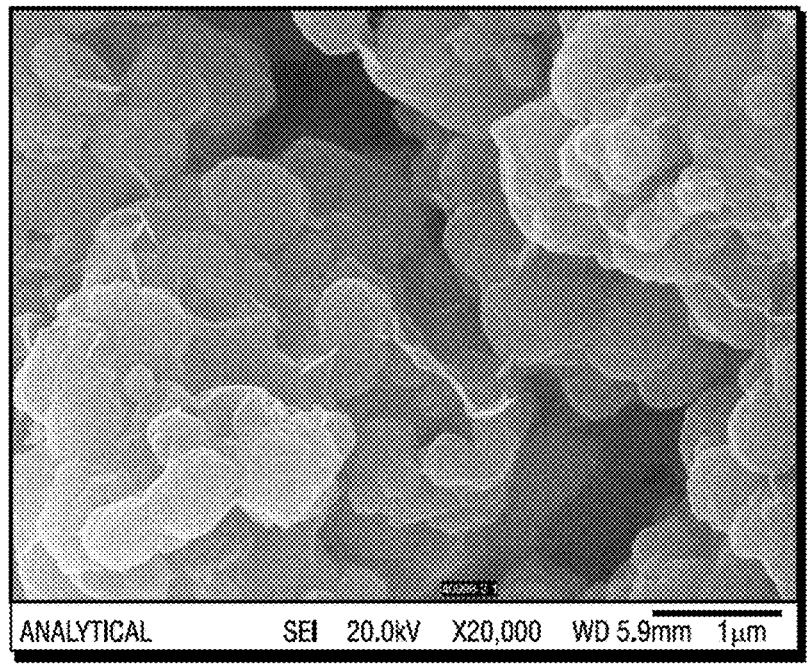
FIG. 6 is a scanning electron microscope photograph of Catalyst B at 20,000 magnification to show the ZSM-5 crystallites.
Figure 7:
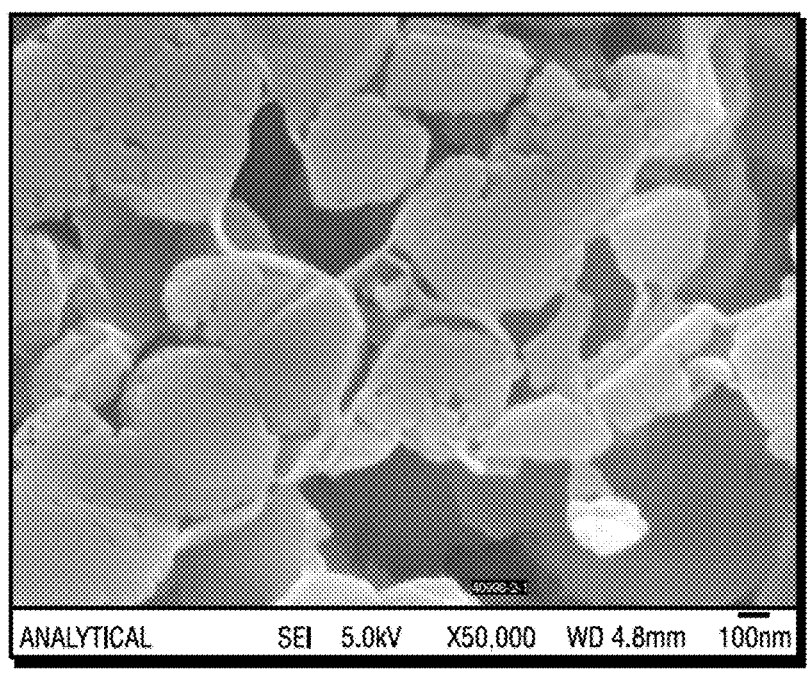
FIG. 7 is a scanning electron microscope photograph of Catalyst B at 50,000 magnification.
Figure 8:
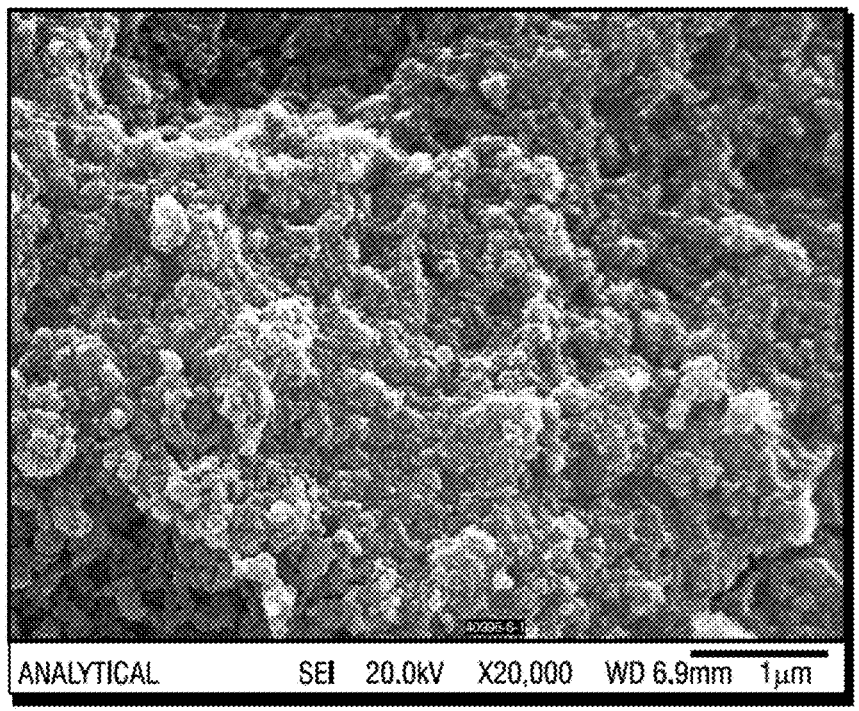
FIG. 8 is a scanning electron microscope photograph of Catalyst C at 20,000 magnification.
Figure 9:
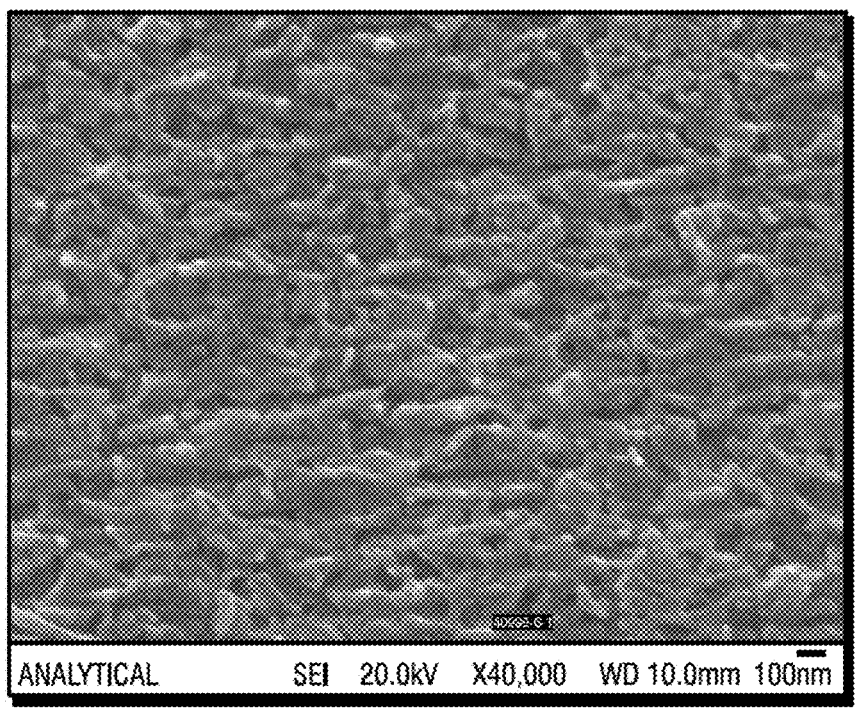
FIG. 9 is a scanning electron microscope photograph of Catalyst C at 40,000 magnification.

As part of the theory of the present invention relates to using ZSM-5 catalyst with substantially larger catalyst pores relative to the micropores of the crystallites, analysis of micropore from ZSM-5 and mesopore in the catalyst extrudates was performed by Argon adsorption at 87K for Catalyst C and Catalyst X catalysts. Looking at FIG. 4, the cumulative pore volume is plotted compared to the pore width along the x-axis. The initial volume is based on the crystallites which have a pored width of approximately 5 Angstroms from ZSM-5 crystallites. There appear to be no catalyst pores less than 40 Angstroms and the greatest concentration of pores seem to be around 150 Angstroms. Looking at FIG. 5, the Catalyst X sample has the same basic contribution of cumulative volume from the micropores in the crystallites, but the catalyst pores are much larger have most of the pores around 320 Angstroms in diameter. Density Function Theory measurements of both Catalyst C and Catalyst X are shown in Table 3 below.

TABLE 3

|  | DFT Cumulative Surface Area (m²/g) | | | DFT Cumulative Pore Volume (cm³/g) | | | DFT Pore Size Distribution (Å) | |
| --- | --- | --- | --- | --- | --- | --- | --- | --- |
|  | Total | Micropore | Mesopore | Total | Micropore | Mesopore | Micropore Peak | Mesopore Peak |
| Catalyst C | 1194 | 1077 | 117 | 0.592 | 0.147 | 0.445 | 5.2 | ~150 |
| Catalyst X | 1354 | 1253 | 101 | 0.643 | 0.174 | 0.47 | 5.2 | ~330 |

Based on the improvement of catalyst life and the parameters now known, the combination of small crystallites with large catalyst pores or large mesopores seems to lead to improved catalyst life extending to seven or more days as compared to catalyst life measured in hours.

In closing, it should be noted that the discussion of any reference is not an admission that it is prior art to the present invention, especially any reference that may have a publication date after the priority date of this application. At the same time, each and every claim below is hereby incorporated into this detailed description or specification as additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

REFERENCES

All of the references cited herein are expressly incorporated by reference. The discussion of any reference is not an admission that it is prior art to the present invention, especially any reference that may have a publication data after the priority date of this application. Incorporated references are listed again here for convenience:

1. Zeolites, 1994, Vol 14, November December "Synthesis of ZSM-5 Zeolite with Small Crystal Size and its Catalytic Performance for Ethylene Oligomerization" Yamamura et al.

The invention claimed is:

1. A process for oligomerizing ethylene to produce transportation fuel products comprising:

oligomerizing ethylene in a reactor with a fixed bed of catalyst at a pressure of between 0 psig and 800 psig, a temperature of between 260° C. and 420° C., a gas hourly space velocity of between 1000 and 5000 $h^{-1}$, and an ethylene conversion of at least 85% to produce the transportation fuel products;

wherein the catalyst is free of catalyst metals other than silica and alumina, and the catalyst comprises a binder and ZSM-5 crystallites with a mean length of less than 150 nm, has a micropore volume greater than 0.08 ml/g and a total pore volume greater than 0.60 ml/g, is characterized by a ratio of total surface area to micropore surface area of 1.08 or less and a ratio of external surface area to micropore surface area of 0.54 or less.

2. The process according to claim 1 wherein the catalyst has an external surface area of at least 135 $m^2/g$.

3. The process according to claim 1 wherein the ethylene conversion is 90% for at least 170 hours without regeneration of the catalyst.

4. The process according to claim 1 wherein the ZSM-5 crystallites are situated within the binder of the catalyst and wherein the binder has mesopores for the reactants to access the crystallites and micropores within the crystallites, and further wherein the ratio of pore volume in the mesopores relative to the pore volume in the micropores is at least 1.5 to 1.

5. The process according to claim 1 wherein the ZSM-5 crystallites are situated within the binder of the catalyst and wherein the binder has mesopores for the reactants to access the crystallites and micropores within the crystallites, and further wherein the ratio of pore volume in the mesopores relative to the pore volume in the micropores is at least 2 to 1.

* * * * *